US010288542B2

(12) United States Patent
Mishra et al.

(10) Patent No.: US 10,288,542 B2
(45) Date of Patent: May 14, 2019

(54) DEVICE, APPARATUS AND METHOD FOR DETERMINING PARTICLE SIZE DISTRIBUTION

(71) Applicants: Anant Kumar Mishra, Bangalore (IN); Naveen Kumar Ssm, Bangalore (IN)

(72) Inventors: Anant Kumar Mishra, Bangalore (IN); Naveen Kumar Ssm, Bangalore (IN)

(73) Assignee: Siemens Healthcare Diagnostics Inc., Tarrytown, NY (US)

(*) Notice: Subject to any disclaimer, the term of this patent is extended or adjusted under 35 U.S.C. 154(b) by 469 days.

(21) Appl. No.: 15/013,529

(22) Filed: Feb. 2, 2016

(65) Prior Publication Data

US 2017/0219472 A1   Aug. 3, 2017

(51) Int. Cl.
| G01N 15/00 | (2006.01) |
| G01N 15/02 | (2006.01) |
| G06K 9/00 | (2006.01) |
| G01N 15/04 | (2006.01) |
| G01N 15/10 | (2006.01) |
| G01N 1/40 | (2006.01) |

(52) U.S. Cl.
CPC ......... *G01N 15/0227* (2013.01); *G01N 15/04* (2013.01); *G06K 9/00134* (2013.01); *G01N 15/02* (2013.01); *G01N 15/0205* (2013.01); *G01N 15/10* (2013.01); *G01N 2001/4083* (2013.01); *G01N 2015/1075* (2013.01)

(58) Field of Classification Search
CPC ......... G01N 15/02; G01N 15/04; G01N 15/10
USPC ......................................... 348/79
See application file for complete search history.

(56) References Cited

U.S. PATENT DOCUMENTS 5,974,901 A * 11/1999 Zborowski ............ G01N 15/10
                                                  73/865.5
6,553,849 B1 * 4/2003 Scofield ............ G01N 15/0266
                                                   324/71.1

FOREIGN PATENT DOCUMENTS

| CN | 103006248 A | 4/2013 |
| DE | 10239767 A1 | 3/2004 |

* cited by examiner

*Primary Examiner* — Jeffery A Williams
(74) *Attorney, Agent, or Firm* — Lempia Summerfield Katz LLC

(57) ABSTRACT

An imaging device for determining particle size distribution including a sample receptacle containing a sample and an imager capable of capturing a plurality of images of the sample in a region of observation. The imaging device further includes a radiation source provided linearly opposite to the imager and a base platform that supports the imager and the radiation source.

16 Claims, 6 Drawing Sheets

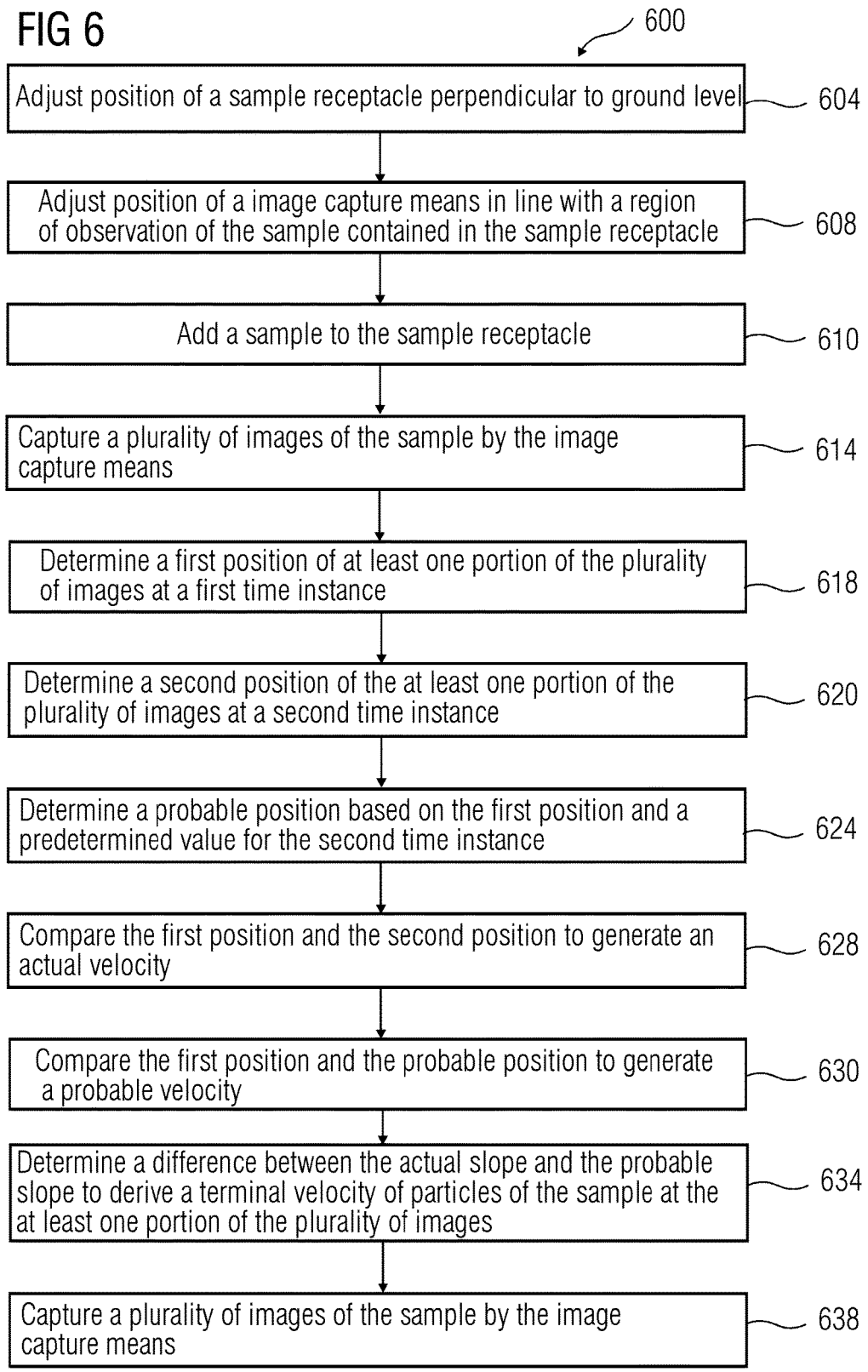

DEVICE, APPARATUS AND METHOD FOR DETERMINING PARTICLE SIZE DISTRIBUTION

TECHNICAL FIELD

The present embodiments relate to measurement of particle size distribution, and more particularly to determining particle velocities for determining particle size distribution.

BACKGROUND

Particle size distribution measurement is employed to monitor and control particle size in an industrial environment. For example, in pharmaceutical, metallurgy or chemical manufacturing industries, particle size distribution plays a crucial role in monitoring a product' s quality.

Particle size distribution can be measured using many techniques, based on an anticipated size of a particle. Existing techniques include scanning electron microscopy (SEM), field emission scanning electron microscopy, laser diffraction, and dynamic light scattering. In certain techniques, samples are directly injected into a test sample and the particle size distribution of the samples is measured. Such techniques invariably require high precision equipment that may be expensive.

Another commonly used technique is sedimentation, in which the sedimentation properties of the particles are analyzed. This technique typically works on principles of X-ray diffraction or microscopy, and may require trained operators for its usage. Further, the equipment may have to be regularly upgraded to ensure that accuracy of the measured particle size distribution is maintained. Therefore, the current equipment to measure particle size distribution are expensive and have complex components.

SUMMARY

The scope of the present invention is defined solely by the appended claims and is not affected to any degree by the statements within this summary.

The present embodiments may obviate one or more of the drawbacks or limitations in the related art. For example, an imaging device for determining particle size distribution is disclosed herein. The imaging device includes a sample receptacle containing a sample and an imager capable of capturing a plurality of images of the sample in a region of observation. The imaging device also includes a radiation source provided linearly opposite to the imager. Further, the imaging device includes a base platform that supports the sample receptacle, the imager, and the radiation source.

An apparatus for determining particle size distribution is also disclosed herein. The apparatus includes an imaging device including an imager capable of capturing a plurality of images of a sample. The imaging device is communicatively coupled to a computing unit. The computing unit includes a processor having an analyzer configured to determine a first position at a first time instance and a second position at a second instance of at least one portion of the plurality of images. The at least one portion represents at least one particle of the sample. The processor also includes a prediction unit configured to predict a probable position for the second time instance based on the first position and a predetermined value. Further, the processor includes a comparator that compares the first position and the second position to generate an actual velocity, and that compares the first position with the probable position to generate a probable velocity. The processor also includes a subtractor to determine a terminal velocity of particles of the sample at the at least one portion based on a difference between the actual velocity and the probable velocity, and a calculator to determine the particle size distribution using the terminal velocity.

Further, a method is disclosed for determining the particle size distribution. The method includes capturing a plurality of images of a sample contained in a sample receptacle by an imager. The method includes determining a first position of at least one portion of the plurality of images at a first time instance and determining a second position of the at least one portion of the plurality of images at a second time instance. The at least one portion of the plurality of images represents at least one particle of the sample. The method further includes predicting a probable position based on the first position and a predetermined value. The method also includes comparing the first position and the second position to generate an actual velocity and comparing the first position and the probable position to generate a probable velocity. The method further includes the act of determining a terminal velocity of particles of the sample at the at least one portion of the plurality of images based on a difference between the actual slope and the probable slope. The method calculates the particle size distribution from the terminal velocity.

BRIEF DESCRIPTION OF THE DRAWINGS

FIG. 6 illustrates one embodiment of a method for determining the particle size distribution.

DETAILED DESCRIPTION

Figure 1:
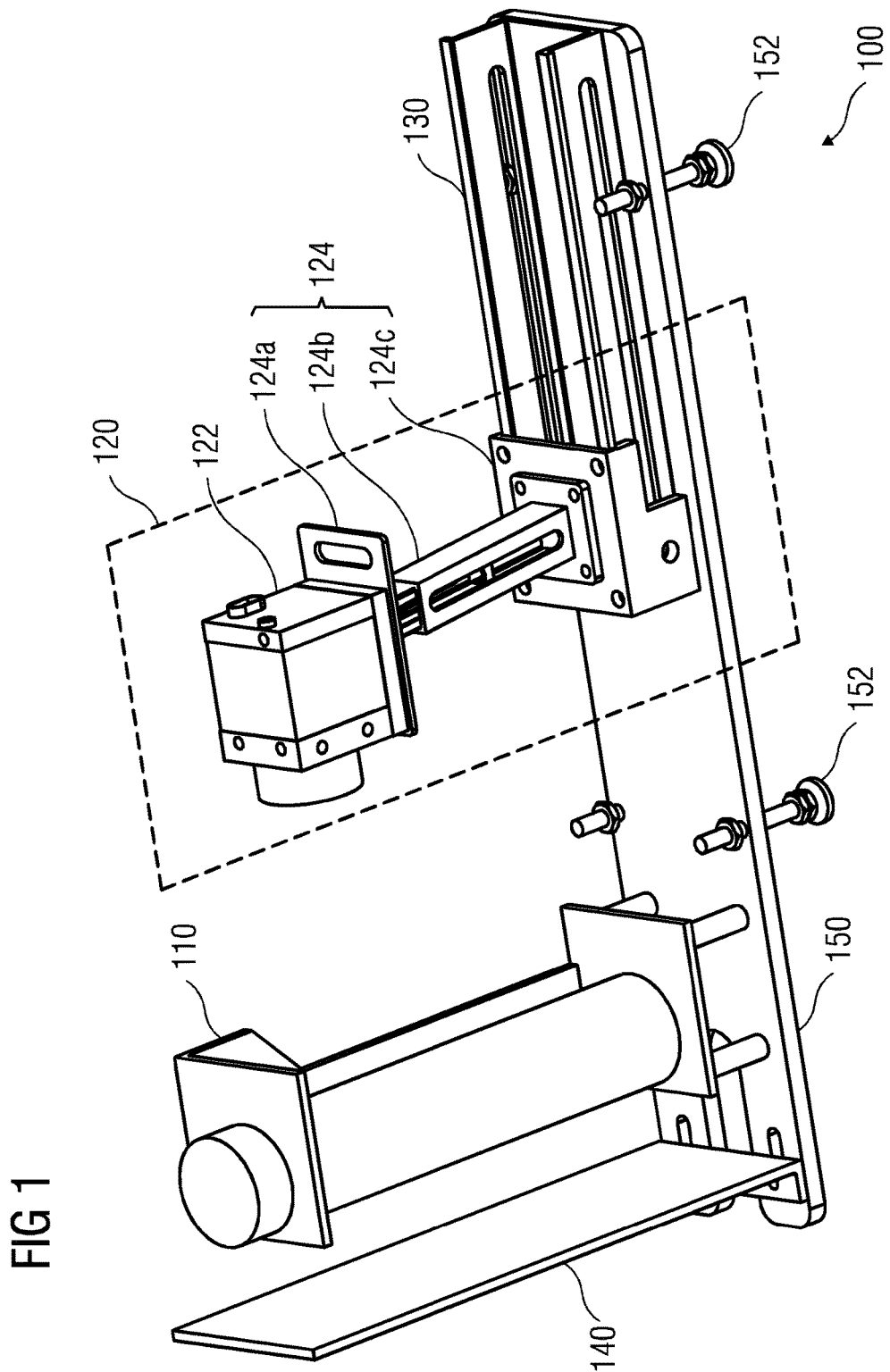
FIG. 1 exemplarily illustrates an isometric view of an imaging device of an apparatus for determining particle size distribution.

FIG. 1 illustrates an isometric view of an imaging device 100 of the apparatus for determining particle size distribution of a sample. For example, the sample includes a solid substance, such as powders used in pharmaceutical, metallurgy or chemical manufacturing industries. In an exemplary embodiment, the sample is a nano powder, such as chromium dioxide. The sample may also include a liquid substance, such as peptides and proteins. In another embodiment, the sample may be divided into 3 primary regions (e.g., an upper region, a middle region and a bottom region). The upper region is toward an opening of a sample receptacle containing the sample (not depicted in FIG. 1). The bottom region is toward a closed end of the sample receptacle. Further, the middle region is a central region of the sample where the effect of the gravitational force on particles of the sample is most palpable. Therefore, the middle region may be referred to as region of observation.

Figure 2:
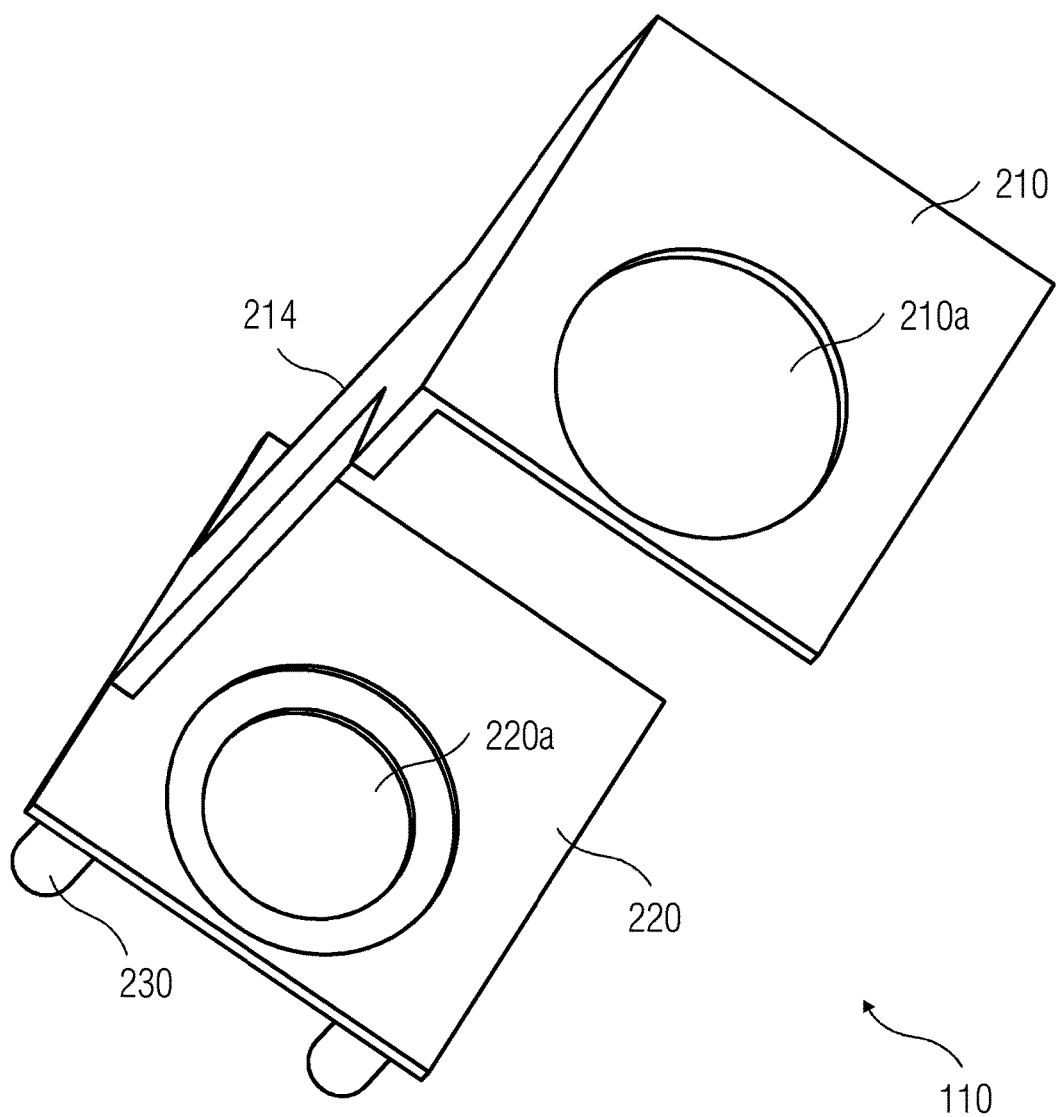
FIG. 2 exemplarily illustrates an isometric view of a receptacle enclosure of the imaging device illustrated in FIG. 1.

The sample receptacle of the imaging device 100 includes transparent laboratory glassware (e.g., test tubes and the like). In the present embodiment, the sample receptacle is a standard test tube, however the size of the sample receptacle may vary based on the sample. The sample receptacle is placed in a receptacle enclosure 110 as depicted in FIG. 2. The receptacle enclosure 110 holds the sample receptacle (not depicted in the FIG. 2) perpendicular to a base platform 150. The receptacle enclosure 110 includes a top plate 210, a bottom plate 220 and four legged support 230. The top plate 210 has a top opening 210a with a diameter more than the outer diameter of the sample receptacle. The top opening 210a may also be provided with a sponge to prevent scratches on the sample receptacle. The top plate 210 and the bottom plate are connected to each other by a connector 214. The bottom plate 220 rests on the four legged support 230. The bottom plate 220 has a bottom opening 220a with a diameter greater than an outer diameter of the sample receptacle. In the present embodiment, the diameter of the opening 220a is 0.1 mm greater than the outer diameter of the sample receptacle. Further, the bottom plate 220 may be built depending on the type of sample receptacle. For example, in the present embodiment the bottom plate 220 is built to support flat based sample receptacles.

The imaging device 100 also includes a guide 130 and an image capture assembly 120. The guide 130 enables the image capture assembly 120 to move in forward and backward (i.e., toward and away from the receptacle enclosure 110). The image capture assembly 120 includes an imager 122 and a support 124 as depicted in FIG. 3.

Figure 3:
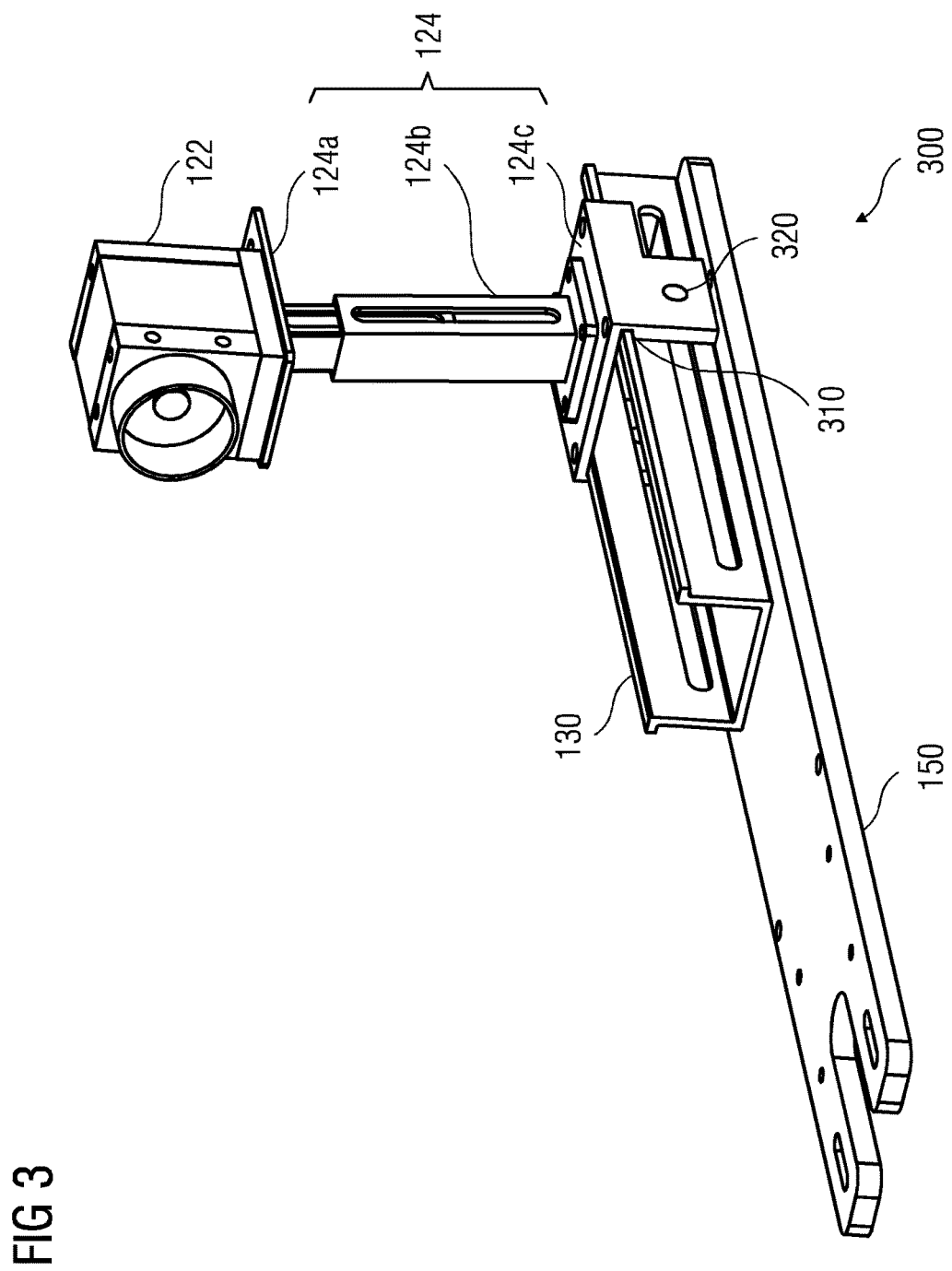
FIG. 3 exemplarily illustrates an isometric view of an image capture assembly.

FIG. 3 exemplarily illustrates an isometric view of the image capture assembly 300. FIG. 3 also depicts the guide 130 that enables the forward and backward movement of the imager 122. As depicted in the FIG. 3, the imager 122 is provided on the support 124 that facilitates alignment of the imager 122 with the region of observation of the sample. In an example embodiment, the support 124 includes an upper mounting plate 124a that receives the imager 122 and a vertical slide 124b extending from the upper mounting plate 124a toward the guide 130. The vertical slide 124b is used to adjust a height of the imager 122 depending on the type of sample receptacle used. The support 124 also includes a lower sliding plate 124c that slides along an axis of the guide 130. The lower sliding plate 124c rests on the guide 130 by a groove 310. The groove 310 provides that the lower sliding plate 124c moves along the axis of the guide 130. The lower sliding plate 124c also includes through slots 320 and locking screws to fix the lower sliding plate 124c to the guide 130. The imager 122 may include a charge-coupled device image sensor or a Complementary Metal-Oxide-Semiconductor (CMOS) sensor for capturing images of the sample. In the present example, the imager 122 is a CMOS sensor.

Further, the imaging device 100 includes a radiation source 140 that is a uniform light provided linearly opposite to the imager 122. The radiation unit is provided in close proximity to the receptacle enclosure 110 housing the sample receptacle. The distance between the receptacle enclosure 110 and the radiation unit 140 is minimized to prevent surface reflections. In the present embodiment, the radiation source 140 is an electromagnetic beam having a wavelength of 620-780 nm. The wavelength of 620-780 nm may be used as the dispersion for higher wavelengths and is lesser than that of lower wavelengths. Because dispersion is less, the smaller particles may be clearly observed.

Additionally, the imaging device 100 includes the base platform 150 that supports the receptacle enclosure 110, the guide 130 and the radiation source 140. The base platform 150 further includes leveler 152 to adjust the imager 122 and the receptacle enclosure 110 perpendicular to ground level. The perpendicular position of the receptacle enclosure 110 provides that the effect of gravitational force on the particles of the sample is maintained uniformly. Also, because the particle size distribution is determined based on the principle of sedimentation, inclination of the sample receptacle changes the direction of the sedimentation (e.g., inclination may cause the particles in the sample to settle on an inner surface of the sample receptacle and slide along the inner surface). This tendency upsets the sedimentation of the particles and may result in incorrect readings. Accordingly, the base platform 150 is provided with leveling screws 152 that decrease inclination in the sample receptacle housed in the receptacle enclosure 110.

Figure 4:
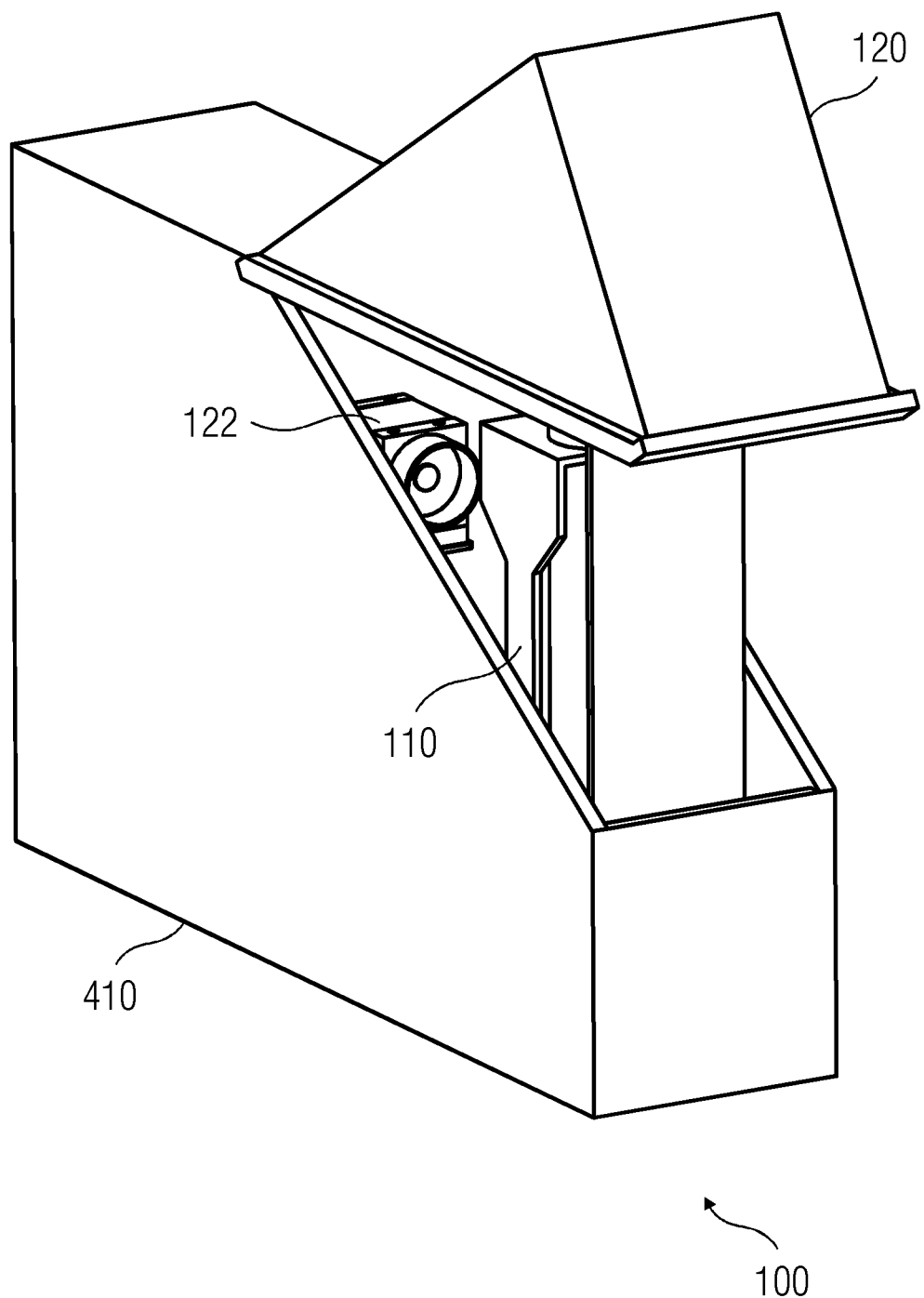
FIG. 4 exemplarily illustrates an isometric view of a housing of the imaging device illustrated in FIG. 1

The imaging device 100 further includes a housing as depicted in FIG. 4. FIG. 4 exemplarily illustrates an isometric view of the housing 410. As depicted in the figure, the housing 210 encloses the receptacle enclosure 110, the image capture assembly 120, the radiation unit 140, the base platform 150 along with the guide 130, and the leveler 152. In an example embodiment, the housing 410 is fixed to the base platform 150 by protruding clamps internal on an inside surface of the housing 410. The housing 410 is provided with a lid 420 to insert or remove the sample receptacle from the receptacle enclosure 110. The lid 420 provides optical isolation to provide that the images of the sample are captured free from any interference due to ambient lights. Additionally, the housing 410 may be in a cubical in shape for ease in setting up the imaging device 100 in compact places.

The imaging device 100 and its components are designed considering manufacturability. The components may be easily manufactured using sheet metal and without complex contours that require special machines to manufacture. Further, non-complex components used, such as CMOS sensors, make the manufacturing cost of the imaging device relatively minimum. Also, as depicted in FIGS. 1-4, assembly of the components of the imaging device 100 is very simple.

Figure 5:
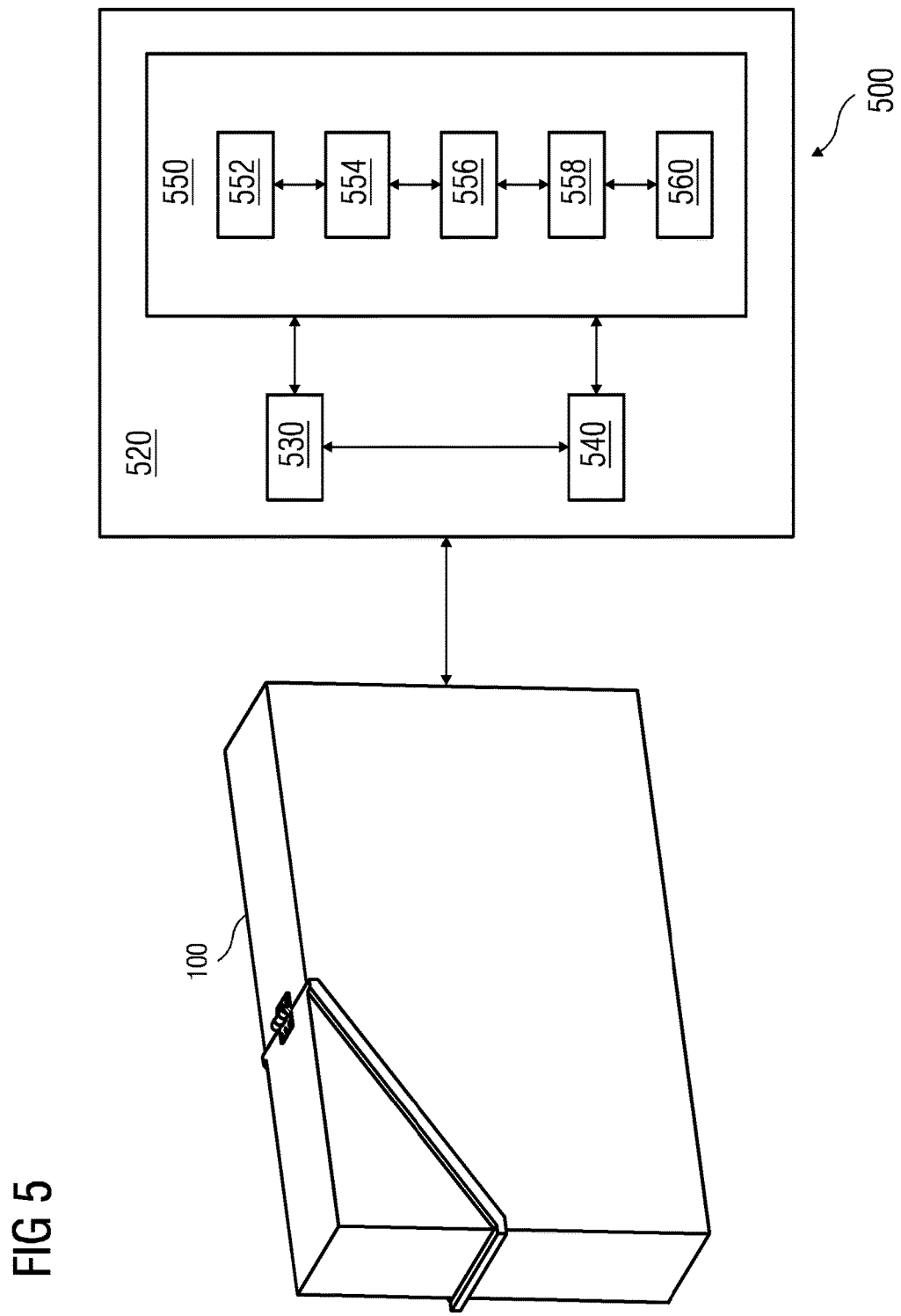
FIG. 5 illustrates one embodiment of a block diagram of the apparatus for determining particle size distribution.

FIG. 5 illustrates a block diagram of the apparatus 500 for determining particle size distribution of the sample. The apparatus 500 includes the imaging device 100 and a computing unit 520. The computing unit 520 is personal computer, laptop or any hand-held device (e.g., such as mobile phone). In the present embodiment, the computing unit 520 is a personal computer. The imaging device 100 is communicatively coupled to the computing unit 520 using a communication network that includes wired and/or wireless connectivity employing known technologies. For example, wired communication networks may include Ethernet communications and universal serial bus (USB) interfaces, and wireless networks may include Wi-Fi communications, cellular communications, Bluetooth, and the like.

The computing unit 520 includes a memory 530, a communication module 540 and a processor 550. The communication module 540 receives images of the sample captured by the imager 122 of the imaging device 100. The memory 530 includes a non-volatile memory and a random access memory (RAM) that store each of the images of the sample with a corresponding timestamp. The non-volatile memory and RAM of the memory 530 are also used to store an image-processing algorithm.

The processor 550 of the computing unit 520 executes the image-processing algorithm to determine the particle size distribution of the sample by an analyzer 552, a prediction unit 554, a comparator 556, a subtractor 558 and a calculator 560. The images stored in the memory 530 are analyzed based on the timestamp of each of the images by the analyzer 552. The analyzer 552 determines a particle position of one or more particles of the sample by determining a position of a portion of the image. The portion of the image corresponds to one or more particles of the sample. The timestamp of each of the images is used to determine the position of the portion for a particular time instance. In an embodiment, the position of the portion of the image may vary in each of the image for different time instances. The difference in the position of portion is determined by the analyzer 552. For example, the analyzer 552 determines a first position ($p_1$) of the portion of a first image at a first time instance ($t_1$) and a second position ($p_2$) of the portion from a second image at a second time instance ($t_2$).

In addition to determining the position of the portion of the particles, the processor 550 predicts a probable position of the portion by the prediction unit 554. The prediction unit 554 predicts the probable position of the portion for the second time instance ($t_2$) based on the first position ($p_1$) and a predetermined value. The predetermined value is determined based on the principle of Stoke's law. Accordingly, the predetermined value is determined by the gravitational force on the particles of the sample. Further, in the certain embodiments, the sample may be added to a dispersion medium. Therefore, the predetermined value is also determined by a dispersion medium viscosity and a dispersion medium density of the dispersion medium in which the sample is added.

The processor 550 further compares the first position ($p_1$) and the second position ($p_2$) by the comparator 556 to generate an actual velocity. The comparator 556 also compares the first position ($p_1$) and the probable position to generate a probable velocity. The actual velocity and the probable velocity are then subtracted by the subtractor 558 to derive a terminal velocity of the particles represented in the at least one portion of the plurality of images. The processor 550 calculates the particle size distribution from the terminal velocity by the calculator 560. The calculator 560 is configured to apply the principle of Stoke's law while determining the particle size distribution.

The apparatus 500 may be operated in two stages: a calibration stage; and a testing stage. The operation for both the stages includes connecting the imaging device 100 to the computing unit 520. In an embodiment, the imaging device 100 is connected to the computing unit 520 by a USB cable. In the calibration stage, the dispersion medium is added to the sample receptacle placed in the receptacle enclosure 110. The sample is not added in the calibration stage. The analyzer 552 of the processor 550 is configured to adjust brightness of the images captured by the imager 122. Further, the lower sliding plate 124a adjusts the position of the imager 122 on the guide 130 in order to obtain optimal brightness of the images. Furthermore, the height of imager 122 is adjusted in line with the region of observation. The analyzer 552 then stores the calibrated settings in the memory 530.

The calibrated settings are used to preset the imaging device 100 and the computing unit 520 prior to the testing stage. In the testing stage, the sample is added to the dispersion medium and mixed thoroughly. A period of observation is input to the computing unit 520, and the processor 550 calculates the particle size distribution by executing the image-processing algorithm. The apparatus 500 is configured to operate in the calibration stage after the completion of each test stage, such that any alteration in calibrated settings is determined. In an embodiment, a transparency of the dispersion medium is altered after the test stage. The analyzer 552 assesses the alteration in the transparency of the dispersion medium and creates an alert for an operator. Therefore, the required operator skill set for the usage of the apparatus 500 is limited to basic skill for operation of a general purpose computer.

FIG. 6 illustrates a method 600 for determining the particle size distribution using an apparatus 500 exemplarily illustrated in FIG. 5 for a sample. The sample may be divided into 3 primary regions: an upper region; a middle region; and a bottom region. The upper region may be toward an opening of a sample receptacle containing the sample (not depicted in FIG. 1). The bottom region may be toward a closed end of the sample receptacle. In the method 600, at act 604, the position of a sample receptacle is adjusted perpendicular to ground level. In an example embodiment, a leveler 152 is used to adjust a base platform 150 in line with the ground level. Further, a receptacle enclosure 110 is configured to hold the sample receptacle perpendicular to the base platform 150. At act 608, the position of an imager 122 is adjusted in line with a region of observation of the sample contained in the sample receptacle. In an example embodiment, the region of observation is the middle region of the sample where the effect of the gravitational force on particles of the sample is most palpable. In another example embodiment, the entire sample is considered as the region of observation and a relative state space is generated for every image to reduce the overall error for every image.

At act 610 of the method 600, the sample is added to the sample receptacle 110. In an exemplary embodiment, the sample is added to a dispersion medium present in the sample receptacle. In another embodiment, the sample may include magnetized particles. At act 610, prior to adding the sample to the sample receptacle, the sample placed in the sample receptacle is demagnetized. Further, the sample receptacle is configured to distribute the effect of the magnetized particles on the non-magnetized particles. For example, the sample receptacle is configured with a wide, closed end to distribute the effect of the magnetized particles on the non-magnetized particles. Alternatively, the sample receptacle is configured as a test tube bent near the closed end of the sample receptacle.

At act 614, a plurality of images of the sample contained in the sample receptacle is captured by the imager 122. At act 618, a first position ($p_1$) of at least one portion of the plurality of images is determined at a first time instance ($t_1$). In the present embodiment, the at least one portion represents one or more particles of the sample. At act 620, a second position ($p_2$) of the at least one portion of the plurality of images is determined at a second time instance ($t_2$). At act 624, a probable position is determined based on the first position and a predetermined value for the second time instance ($t_2$). At act 628, the first position ($p_1$) and the second position ($p_2$) is compared to generate an actual velocity. At act 630, the first position ($p_1$) and the probable position are compared to generate a probable velocity.

The method 600 further discloses that at act 634, a difference between the actual slope and the probable slope is determined to derive a terminal velocity of particles of the sample at the at least one portion of the plurality of images. At act 638, the particle size distribution is calculated from the terminal velocity by applying the principle of Stoke's law.

The foregoing examples have been provided merely for the purpose of explanation and are in no way to be construed as limiting of the method 600, imaging device 100 and the apparatus 500 disclosed herein. While the method 600, the imaging device 100 and the apparatus 500 have been described with reference to various embodiments, it is understood that the words, which have been used herein, are words of description and illustration, rather than words of limitation. Further, although the method 600, the imaging device 100 and the apparatus 500 have been described herein with reference to particular means, materials, and embodiments, the method 600, imaging device 100 and the apparatus 500 are not intended to be limited to the particulars disclosed herein; rather, the method 600, imaging device 100 and the apparatus 500 extend to all functionally equivalent structures, methods and uses, such as are within the scope of the appended claims. Those skilled in the art, having the benefit of the teachings of this specification, may effect numerous modifications thereto and changes may be made without departing from the scope and spirit of the method and the apparatus 500 disclosed herein in their aspects.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. An apparatus for determining particle size distribution, the apparatus comprising:
    an imaging device comprising an imager for capturing a plurality of images of a sample; and
    a computing unit communicatively coupled to the imaging device, the computing unit comprising:
        a processor comprising:
            an analyzer configured to determine a first position at a first time instance and a second position at a second time instance of at least one particle of the sample within at least one portion of the plurality of images;
            a prediction unit configured to predict a probable position of the at least one particle for the second time instance based on the first position of the at least one particle and a predetermined value, wherein the predetermined value is determined based on a gravitational force of particles of the sample, a dispersion medium viscosity of a dispersion medium in which the sample is added, a dispersion medium density of the dispersion medium in which the sample is added, or a combination thereof;
            a comparator configured to calculate an actual velocity of the at least one particle based on the first position of the at least one particle at the first time instance and the second position of the at least one particle at the second time instance, and to calculate a probable velocity of the at least one particle based on the first position of the at least one particle at the first time instance and the probable position of the at least one particle at the second time instance;
            a subtractor configured to determine a terminal velocity of particles of the sample in the at least one portion of the at least one image by calculating a difference between the actual velocity and the probable velocity; and
            a calculator configured to determine the particle size distribution using the terminal velocity.

2. The apparatus of claim 1, wherein the imaging device comprises:
    a receptacle enclosure to hold a sample receptacle that contains the sample;
    a base platform that supports the receptacle enclosure, the base platform having at least one leveler; and
    a housing that encloses the base platform and the receptacle enclosure.

3. The apparatus of claim 2, wherein the imaging device further comprises:
    a guide mounted on the base platform; and
    an image capture assembly mounted on the guide, the image capture assembly comprising the imager and a support.

4. The apparatus of claim 1, wherein the imaging device further comprises:
    a radiation source mounted on a base platform linearly opposite to the imager.

5. A method for determining particle size distribution comprising:
    capturing a plurality of images of a sample contained in a sample receptacle with an imager;
    determining a first position of at least one particle within at least one portion of the plurality of images at a first time instance;
    determining a second position of the at least one particle within the at least one portion of the plurality of images at a second time instance;
    predicting a probable position of the at least one particle based on the first position of the at least one particle and a predetermined value, wherein the predetermined value is determined based on a gravitational force of particles of the sample, a dispersion medium viscosity of a dispersion medium in which the sample is added, a dispersion medium density of the dispersion medium in which the sample is added, or a combination thereof;
    calculating an actual velocity of the at least one particle based on the first position of the at least one particle at the first time instance and the second position of the at least one particle at the second time instance;
    calculating a probable velocity of the at least one particle based on the first position the at least one particle at the first time instance and the probable position of the at least one particle at the second time instance;
    determining a terminal velocity of particles of the sample in the at least one portion of the at least one image by calculating a difference between the actual velocity and the probable velocity; and
    calculating the particle size distribution from the terminal velocity.

6. The method of claim 5 further comprising:
    adjusting the sample receptacle perpendicular to ground level; and
    adjusting position of the imager in line with a region of observation of the sample contained in the sample receptacle.

7. The method of claim 5, wherein the sample comprises magnetized particles and non-magnetized particles suspended in the dispersion medium.

8. The method of claim 7 further comprising:
demagnetizing the sample placed in the sample receptacle; and
distributing an effect of the magnetized particles over the non-magnetized particles.

9. The apparatus of claim 1, wherein the imaging device further comprises:
a sample receptacle containing a sample;
a radiation source provided linearly opposite to the imager; and
a base platform that supports the imager and the radiation source.

10. The apparatus of claim 9, wherein the sample in the sample receptacle comprises an upper region, a middle region and a bottom region, wherein the middle region is the region of observation of the sample.

11. The apparatus of claim 9, wherein the radiation source is configured to produce an electromagnetic beam of wavelength 620-780 nm.

12. The apparatus of claim 9, wherein the base platform is provided with at least one leveler.

13. The apparatus of claim 9, further comprising:
a guide mounted on the base platform; and
an image capture assembly mounted on the guide, the image capture assembly comprising the imager and a support.

14. The apparatus of claim 13, wherein the support further comprises:
an upper mounting plate that receives the imager;
a vertical slide extending from the upper mounting plate towards the guide; and
a lower sliding plate that slides along an axis of the guide.

15. The apparatus of claim 13, further comprising:
a receptacle enclosure to hold the sample receptacle that contains the sample; and
a housing that encloses the base platform, the receptacle housing, the guide and the image capture assembly.

16. The apparatus of claim 1, wherein the imager is a complementary metal-oxide-semiconductor (CMOS) sensor.

* * * * *